United States Patent

Kankkunen et al.

[11] Patent Number: 5,572,992
[45] Date of Patent: Nov. 12, 1996

[54] METHOD AND APPARATUS FOR IDENTIFYING AN ANESTHETIC FLUID CONTAINER AND/OR FOR DETECTING A CONNECTION BETWEEN THE CONTAINER AND A CONDUIT SUPPLYING A GAS TO A PATIENT

[75] Inventors: Jukka Kankkunen, Helsinki; Pertti Puukangas, Espoo, both of Finland

[73] Assignee: Instrumentarium Corp., Finland

[21] Appl. No.: 397,611

[22] Filed: Mar. 2, 1995

[30] Foreign Application Priority Data

Mar. 4, 1994 [FI] Finland .................................. 941059

[51] Int. Cl.⁶ .................................................. A61M 16/00
[52] U.S. Cl. ................... 128/203.14; 128/202.27; 128/203.12
[58] Field of Search .................... 128/203.12, 203.14, 128/203.16, 203.17, 203.25, 203.26, 203.27, 202.27, 200.24; 261/39.1, 96, 99, 105, DIG. 65

[56] References Cited

U.S. PATENT DOCUMENTS

| | | | |
|---|---|---|---|
| 3,920,149 | 11/1975 | Fortino et al. | 222/1 |
| 4,627,695 | 12/1986 | Beauviala et al. | 352/72 |
| 4,912,512 | 3/1990 | Midorkawa et al. | 355/260 |
| 5,293,865 | 3/1994 | Altner et al. | 128/203.12 |

FOREIGN PATENT DOCUMENTS

| | | |
|---|---|---|
| 0338518 | 10/1989 | European Pat. Off. . |
| 37 06 307 | 5/1988 | Germany ............... 400/207 E |
| 61-22972 | 1/1986 | Japan ..................... 400/207 E |
| 2177007 | 1/1987 | United Kingdom . |
| 2254005 | 9/1992 | United Kingdom . |
| WO92/19305 | 11/1992 | WIPO . |
| WO93/10392 | 5/1993 | WIPO . |

*Primary Examiner*—Edgar S. Burr
*Assistant Examiner*—Eric P. Raciti
*Attorney, Agent, or Firm*—Andrus, Sceales, Starke & Sawall

[57] ABSTRACT

An apparatus and method for identifying containers (1) containing different anesthetic fluids. A connecting element (8) is used for coupling the container with a conduit (6) extending to a patient for supplying an anesthetic to a patient. The containers containing anesthetic fluids are designated or labeled distinctly from each other by means of at least one magnetic-field producing element (12). The presence of this element is in turn detected by means of a magnetic-field detecting element (13). The identification of a container containing an anesthetic fluid and, thus, an anesthetic fluid contained therein is effected by means of an identification element (15), which receives a signal from one or more magnetic-field detecting elements. The detection can also be used as a basis for establishing whether the container is coupled in its position.

25 Claims, 1 Drawing Sheet

METHOD AND APPARATUS FOR IDENTIFYING AN ANESTHETIC FLUID CONTAINER AND/OR FOR DETECTING A CONNECTION BETWEEN THE CONTAINER AND A CONDUIT SUPPLYING A GAS TO A PATIENT

BACKGROUND OF THE INVENTION

The present invention relates to an apparatus for identifying an anesthetic fluid container, said apparatus comprising at least two anesthetic fluid containers, which containers include at least a fluid chamber for an anesthetic fluid and which containers contain anesthetic fluids different from each other in terms of the chemical structure thereof. The apparatus further comprises a gas chamber for vaporizing the anesthetic originating from the fluid chamber and which gas chamber can be a part of the container or a chamber separated from the container. A connecting element couples the container with a conduit extending to a patient for supplying the anesthetic to a patient and which container is detachable from the connecting element and replaceable with another container possibly containing a different anesthetic fluid. A body member installs the container therein in view of coupling it by means of the connecting element with a conduit extending to a patient. The invention relates also to a method for identifying an anesthetic fluid container. Furthermore, the invention relates to a method and apparatus for detecting a connection between an anesthetic container and a conduit supplying a gas to a patient.

BACKGROUND OF THE INVENTION—DESCRIPTION OF THE RELATED ART

The vaporizers generally used in anesthesia, consisting of an anesthetic fluid container and a regulating element, are intended for just one given anesthetic. The user must have a separate vaporizer for each necessary anesthetic. A preferred and easier solution is to use a vaporizer, wherein the regulating element is separated from the anesthetic fluid container and, thus, only the fluid container must be replaced when the anesthetic fluid is to be replaced with another and the regulating element remains the same. The regulating element is used for controlling the flow of a fresh gas delivered to a patient, which flow may occur partially through a gas chamber, in which gas chamber an anesthetic originating from a fluid chamber is vaporized, and which gas chamber may be included in the anesthetic fluid container or separated therefrom, e.g. connected to the regulating element. The regulating element is also used for controlling the flow of an anesthetic vaporized from the anesthetic fluid container to a patient, i.e. for maintaining a desired and safe anesthetic concentration in relation to a fresh gas supplied to a patient. The fresh gas generally consists of a mixture of oxygen and nitrous oxide ($N_2O$) or oxygen and air.

The number of regulating elements required for identifying an anesthetic fluid container is just one, if each anesthetic fluid has its own container element. Another benefit gained by a separate container is that the filling thereof can be easily effected not in the operating room but elsewhere, in a ventilated facility more suitable for the purpose.

Various anesthetic fluids have different vaporizing characteristics and, thus, a regulating element for the anesthetic concentration must operate in a different way on different anesthetic fluids. Thus, the regulating element must be informed that a container containing an anesthetic fluid is coupled therewith. This information can be transmitted by means of mechanical pins or electric contacts (GB 2177007).

When an anesthetic fluid container or a vaporizer is coupled with an anesthesia work station, the work station must be capable of identifying the anesthetic fluid which is contained in this particular container and, preferably, for detecting the presence of said container. If this is done by using pins included in the container or by means of electric contacts, those are susceptible to mechanical failures and soiling. These may lead to error situations, such as the identification of a wrong anesthetic fluid. Due to differences between the vapor pressures of various anesthetic fluids, an incorrect identification. can cause a life-threatening anesthetic concentration. The use of optical means, reflection sensors, opto-forks, electric contacts, connectors and other such methods also involves the hazard of mechanical failures and soiling. When using an optical method, the soiling of an identification spot included in the sensor or container results in the situation that the container is not detected or it is identified incorrectly.

SUMMARY OF THE INVENTION

An object of this invention is to eliminate the above problems. Another object is to provide a simple and reliable apparatus and method for identifying an anesthetic fluid container. A further object is also to provide a method and apparatus for detecting a connection between an anesthetic fluid container and a conduit supplying a gas to a patient.

The characterizing features of an apparatus and method of the invention are set forth in the appended claims.

The invention relates to an apparatus and method suitable for identifying an anesthetic fluid container. The apparatus consists of at least two anesthetic fluid containers, said containers containing anesthetic fluids that are different from each other in terms of the chemical structure. Thus, in the most preferred case, each anesthetic fluid intended for use is provided with its own container. The presently used anesthetic fluids include e.g. halotan, isofluran, enfluran, sevofluran, methoxy fluran and desfluran. Thus, if all these anesthetic fluids are to be used, six different containers are needed.

The selected anesthetic fluid container, which thus includes at least a fluid chamber for an anesthetic fluid but preferably also a gas chamber for vaporizing the anesthetic originating from the fluid chamber, is coupled by means of a connecting element with a conduit extending to a patient for delivering the anesthetic to the patient along said conduit. However, the anesthetic must be mixed with a fresh gas upstream of the respiratory passages of a patient.

The mixing can already be effected e.g. partly in the gas chamber, wherein the anesthetic vaporizes, by delivering through the gas chamber a fresh gas to be administered to a patient, and partly by mixing the mixture of fresh gas and anesthetic discharged from the gas chamber with a fresh gas that has bypassed the gas chamber and is also intended for the patient. Thus, the fresh gas flow usually originating from two different gas sources is preferably divided in two, i.e. a flow passing through and another flow passing by the gas chamber. Subsequently, prior to the administration thereof to a patient, said flows merge together again but contain additionally an anesthetic vaporized from an anesthetic fluid.

According to another presently used mixing method, an anesthetic originating from an anesthetic fluid is vaporized in a gas chamber, wherefrom the vapor, through the action of a produced pressure, pursues along a conduit towards a patient but, upstream of the respiratory passages of the patient, this anesthetic-containing vapor is joined with a fresh gas to be supplied to the patient. Thus, no fresh gas flow is delivered into the gas chamber.

According to the invention, an anesthetic fluid container, intended to be coupled by means of a connecting element with a conduit extending to a patient, must be identified before the anesthetic vaporized from this anesthetic fluid container reaches the respiratory passages of the patient. Thus, it is of a major importance to know that the patient receives exactly the correct anesthetic since, for example, different anesthetics are administered to patients at different concentrations, whereby a flow possibly discharging from the anesthetic container must either be reduced or increased in relation to a fresh gas flow. Another consideration is that the patient may be sensitive to a certain anesthetic, in which case the administration of a wrong anesthetic may cause a life danger.

The identification of an anesthetic fluid container is effected by using magnetic phenomenon. This phenomenon for the identification of anesthetic fluid containers can be exploited in a variety of ways. It is essential that the containers containing different anesthetic fluids be designated differently from each other, whereby the incorrect identification of containers is not possible. The development of magnetic phenomenon requires a magnetic-field producing element, which is usually designated as a magnet, and the detection thereof requires a magnetic-field detecting element, such as e.g. a reed-relay or a Hall-sensor. The number of these elements is dependent on how such elements are to be used in the identification of anesthetic fluid containers. In principle, one magnetic-field producing element and one magnetic-field detecting element are sufficient for distinguishing various anesthetic fluid containers from each other.

The identification could be effected by indicating a certain position in an anesthetic fluid container with a magnetic-field producing element, whereby in each container a certain position refers to a certain anesthetic fluid. In each container containing a different anesthetic fluid, the position would be at a different location. Accordingly, separated from the anesthetic fluid container would be a magnetic-field detecting element for running through the various predetermined positions in an anesthetic fluid container and detection of the existence of a magnetic field in a certain position would be an indication of a certain container containing some anesthetic fluid. An easier solution would be such that would include a number of magnetic-field detecting elements equal to the number of employed anesthetic fluid containers, whereby each possible position of a magnetic-field producing element would be provided with one magnetic-field detecting element. In practice, it would be preferable to include the magnetic-field detecting elements in some solid object, which is here designated as a body member, in such a manner that such elements would place themselves within the sphere of influence of a magnetic-field producing element positioned for each employed container containing a different anesthetic fluid as the anesthetic fluid container and the body member including the magnetic-field detecting elements are brought sufficiently close to each other and placed relative to each other in a position that enables the identification.

According to a preferred exemplary solution, there are several magnetic-field detecting elements separated from a container and an equivalent number of positions included in the containers for placing the magnetic-field producing elements therein. The accepted magnetic combinations are selected in such a manner that the failure of one magnetic-field detecting element does not produce an incorrect identification. Thus, for example, when using four magnetic-field detecting elements, the selected acceptable combinations are those which include an even number of magnetic-field producing elements. If the magnetic-field detecting elements detect an odd number of magnets, it is clear that the question is about a faulty condition. Thus, the method can be applied also in self-diagnostics.

When using four positions included in a container and two magnets per container, it is possible to encode six containers containing different anesthetic fluids if the detection only relates to the number and position of magnets included in the container. If necessary, more alternatives can be introduced by increasing the number of positions.

It is also possible to exploit the polarity of magnets. In that case, magnets are placed in the positions at various attitudes. The magnet can have either its N- or P-pole towards a magnetic-field detecting element which, thus, must be capable of identifying the direction of a magnetic field. In the application of this method, even a single position included in a container can be used for identifying two containers containing different anesthetic fluids. When using several positions, the maximum number of identifiable containers is 2 to the power of N, wherein N is the number of positions.

The magnet can also be mounted at an arbitrary attitude, the identification being effected by measuring the direction of a magnetic field, for example by means of two magnetic-field detecting elements, such as Hall sensors, mounted perpendicularly to each other. Thus, even a single magnet is capable of identifying a variety of alternatives. The limiting factor is principally the accuracy of measurement.

The exploitation of magnetic-field producing and detecting elements does not require any visible or otherwise fault sensitive structures. The magnetic-field producing elements can be e.g. hidden in a fluid container, usually inside its shroud, and the magnetic-field detecting elements respectively outside the container, e.g. inside a body member that the container is to be coupled with as the supply of a vaporized anesthetic originating from the container is commenced to a patient. In order to produce an identification it is sufficient that such elements be brought as close to each other as necessary.

The invention relates also to an apparatus and method for detecting a connection between an anesthetic fluid container and a conduit extending from this container to a patient or a conduit supplying a gas into this container. The coupling of an anesthetic fluid container with a gas-supplying conduit for delivering an anesthetic to a patient is effected by means of a connecting element. Thus, an object of the invention is to detect whether or not a fluid container is coupled on. This is also effected in part by using a magnetic-field producing element and a magnetic-field detecting element. According to the invention, an anesthetic fluid container is indicated by means of a magnetic-field producing element. Although there are a plurality of individual anesthetic fluid containers, possibly even containing different anesthetic fluids, a single magnetic-field producing element will be sufficient for indicating a connection, whereby said element must have such a position in the fluid container that a magnetic-field detecting element spaced apart from the container detects its presence or absence. Thus, the container connection can be detected either from the fact that a magnetic-field detecting element falls within the sphere of influence of a magnetic-field producing element or vice versa, whereby a magnetic-field detecting element lies no longer within the sphere of influence of a magnetic-field producing element.

BRIEF DESCRIPTION OF THE DRAWING

The invention will now be described in more detail with reference made to the accompanying patent drawing, in which.

DESCRIPTION OF THE PREFERRED EMBODIMENT

Figure 1:
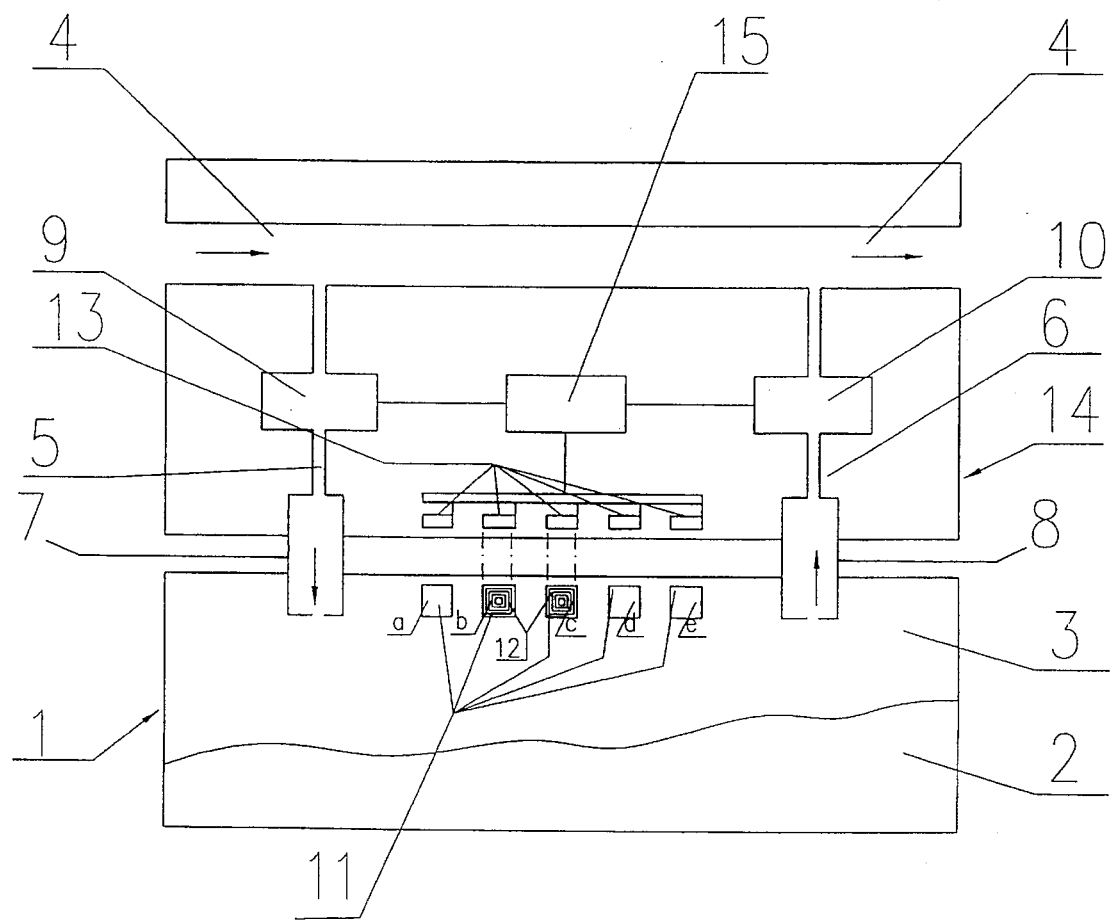
FIG. 1 shows a basic view of the identification of an anesthetic fluid container and an apparatus or a mechanism used therein for detecting the presence of an anesthetic fluid container.

The illustrated apparatus comprises an anesthetic fluid container 1, including a fluid chamber 2 for an anesthetic fluid and a gas chamber 3 for vaporizing an anesthetic therein from the fluid chamber. According to a preferred solution shown in the figure, a gas, such as a fresh gas originating from one or more gas sources, not shown in the figure, is delivered through the gas chamber 3. From the gas source a fresh gas flows along a conduit 4 towards a patient, yet in such a manner that upstream of the patient some of the gas is deflected along another conduit 5 into the gas chamber 3, wherein the fresh gas is admixed with an anesthetic vaporized from the fluid chamber and wherefrom this gas mixture consisting of fresh gas and vapor is carried further along another conduit 6 back into the conduit 4 extending to the patient, wherein the mixture consisting of fresh gas and anesthetic is diluted as far as the anesthetic is concerned upon mixing with the fresh gas flowing along the conduit 4 before the gas mixture reaches the respiratory tracts of a patient. The conduit 5 supplying a gas into and the conduit 6 discharging a gas from the anesthetic fluid container are coupled with the anesthetic fluid container by means of connecting elements 7 and 8. The connecting element can be any useful solution for attaching a conduit either directly or indirectly to a container. Such a connection should be tightly sealed for eliminating gas leaks into the environment.

The conduit 5 is further provided with a valve 9, preferably a shut-off valve, which can be closed and opened as necessary. The conduit 6 extending away from the gas chamber 3 is fitted with a valve 10, preferably a regulating valve, used for regulating the flow discharging from the gas chamber. In addition, the valve 10 is preferably of such a design that allows a flow in just one direction, i.e. from the gas chamber 3 towards a patient.

The anesthetic fluid container includes one or, as shown in the figure, a number of positions 11, which position can be fitted with a magnetic-field producing element 12 required for identifying the container. The purpose is to place preferably one magnetic-field producing element in one position, but usually the arrangement is such that some of the positions remain vacant. In the illustrated solution, the number of positions 11 is five but just two of the stations are fitted with magnetic-field producing elements 12. Outside and spaced from the container 1 is located one or more magnetic-field detecting elements 13. In the figure, the magnetic-field detecting elements are preferably included in a body member 14, which body member is also fitted with the connecting elements 7 and 8. The magnetic-field detecting elements 13 are included in the body member in such a manner that, as the container is coupled by means of the connecting element 8 with the conduit 6 extending to a patient and, preferably at the same time, the container is coupled by means of the connecting element 7 with the conduit 5 supplying fresh gas into the container, the magnetic-field detecting elements fall at this time within the sphere of influence the magnetic-field producing elements possibly included in the container positions 11 but, according to a preferred embodiment, are not within the sphere of influence when the container is not properly connected to the conduit 6. Usually, the magnetic-field producing elements and the magnetic-field detecting elements are aligned with each other at the time of identification in such a manner that one magnetic-field detecting element corresponds to each operative position.

The magnetic-field producing elements and the locations therefor can be selected for example in such a manner that, when using five positions 11 and two magnetic-field producing elements, positions a and b relate to halotan. In that case, each position a and b is provided with a magnetic-field producing element 12 while positions c, d and e are vacant. Accordingly, as the magnetic-field producing elements are included in positions a and c and positions b, d and e are vacant, the container is identified as an enfluran container. In accordance with the same principles, it is also possible to designate containers containing other anesthetic fluids as well.

As shown in the figure, one or more of the magnetic-field detecting elements 13 are in communication with an identification element 15, capable of using information received from each element for identifying which anesthetic fluid is contained in a container that is coupled or is about to be coupled by means of the connecting element 8 with the conduit 6 extending to a patient. Prior to this, the identification element has been supplied with information about which position or positions is or are provided with one or more magnetic-field producing elements 12 corresponding to a container containing whichever anesthetic fluid. Respectively, in view of exploiting the orientation of a magnetic field, the identification element is provided with information about which direction indicates a container containing any given anesthetic fluid. If an identification performed by the identification element indicates that the container assigned to a patient contains a wrong anesthetic fluid, the identification element may produce e.g. an alarm to this effect or close the valve 10 included in the conduit extending from the gas chamber 3 towards a patient or, possibly, close the valve 9 included in the conduit 5 supplying fresh gas into the gas chamber 3.

The replacement of a container with another container carrying either the same anesthetic fluid or some other anesthetic fluid is effected simply by removing the container from one or more connecting elements 8 and 7 said container has been coupled with and by fitting another container in position, the identification of a container being effected at the same time.

The magnetic-field producing element 12 and the magnetic-field detecting element 11 can also be used for detecting a connection between the anesthetic fluid container and the conduit 6 or 5 supplying gas to a patient, i.e. whether or not the container is coupled with the conduit. In practice, the above-described apparatus applicable for the identification of a container can also be used for detecting a connection between a container and a conduit. One magnetic-field producing element, indicating a container, and one magnetic-field detecting element spaced from the container are sufficient. The fall of a magnetic-field detecting element within the sphere of influence of a magnetic-field producing element is an indication of a connection between a container and a conduit. Detection of the presence of a connection may also occur in reversed order, i.e. a magnetic-field detecting element is no longer within the sphere of influence of a magnetic-field producing element. A change in the direction of a magnetic field can also be used as an indication of the existence of a connection. Thus, the identification element 15 must be supplied with information about how to detect whether or not a container is coupled. For example, the identification element produce some type of signal indicating a connection to the operator.

The positions included in the container can be produced e.g. by drilling holes in the container surface or by casting the container in a mould provided with preset locations for the positions. This is followed by placing one or more magnetic-field producing elements in one or more positions, whereafter it is further preferable to secure these elements in their positions and possibly to use e.g. a plastic coating for protecting at least those positions which are provided with magnetic-field producing elements. This way, the magnetic-field producing elements and the positions can be kept clean. Thus, it would also be desirable to prevent the unintentional detachment of these elements or the possible attachment thereof to an incorrect position. In practice, it is beneficial to combine the protection and attachment of magnetic-field producing elements e.g. by casting molten plastics in a position provided with a magnetic-field producing element, said plastics immobilizing the element as it solidifies. The same procedure can be followed when placing the magnetic field detecting elements 13 outside a container in the body member 14.

The invention is by no means limited to the above embodiments but various details of the invention can be modified within the scope of the claims.

In most cases, the anesthetic fluid container includes both a fluid chamber, containing a vaporizable and liquid anesthetic, and a gas chamber for vaporizing some of the fluid. However, this is not absolutely necessary but, instead, the anesthetic fluid container may include just a fluid chamber, whereby the actual gas chamber is a separate element that can be permanently coupled with or be separated from a gas duct extending to a patient. In the invention, the anesthetic fluid container may include not only a fluid chamber and a gas chamber but also an inlet passage for a gas flowing e.g. from gas tanks into and an outlet passage from the gas chamber as well as a passage for a gas flowing from gas tanks to by-pass the gas chamber to a patient, i.e. a classic vaporizer as a whole.

The connecting element need not necessarily be directly coupled with the conduit 5 or 6 but it can also be coupled between the gas chamber and the fluid chamber, especially in the case that the container only includes a fluid chamber but not a gas chamber. Anyway, and even in this case, the container must be regarded as being coupled with the conduit 5 or 6 through the intermediary of a connecting element.

Neither is it necessary to deliver a portion of the fresh gas flow through the gas chamber 3 but, instead, an anesthetic vaporized from the fluid chamber may be forced by the action of a pressure along the conduit 6 towards the conduit 4, the mixing with a fresh gas not being effected until there. In this case, just one connecting element 8 is required.

The above description of the invention has primarily focused on an embodiment, wherein the magnetic-field producing elements are included in a container even when the container is not coupled for operation. However, it is possible to mount the magnetic-field producing elements outside the container, e.g. on a body member, wherein the container can be coupled by means of a connecting element with a gas conduit extending to a patient. In this case, the identification or the coupling of a container could be effected e.g. in such a manner that the magnetic-field producing elements would penetrate into vacant positions provided in the container as each container containing a different anesthetic would only have certain predetermined positions vacant and the magnetic-field detecting elements would detect either those magnetic-field producing elements which are absent or those which are present.

We claim:

1. In anesthesia apparatus, the improvement comprising:
   a body member (14) having a connecting element (8) for detachably connecting an anesthetic container (1) to the apparatus to supply anesthetic to a patient through a conduit connected to the connecting element;
   a selected one of a plurality of anesthetic containers, each of which contains an anesthetic of differing properties, said body member and container being relatively movable to place the container in a position in which the container has a desired operative connection to the connecting element;
   magnetic-field producing means (12) provided in association with each container of said plurality of containers, said magnetic-field producing means establishing a unique magnetic characteristic for each of the containers;
   magnetic-field detecting means (13) provided in association with the body member;
   said magnetic-field producing means (12) and said magnetic-field detecting means (13) being positioned so as to be magnetically couplable when a container is proximate to the body member so that said magnetic-field detecting means detects the magnetic characteristic of said magnetic-field producing means of the container, said magnetic-field producing means and magnetic-field detecting means having a particular magnetic coupling state only when the container is in said operative connection position; and
   an identification element (15) having means for receiving a signal from said magnetic-field detecting means and, in response to the received signal, identifying which one of the plurality of anesthetic containers is proximate to the body member and whether the container is in said operative connection position.

2. The apparatus according to claim 1 wherein said magnetic-field producing means and said magnetic-field detecting means are provided on said container and body member, respectively, so as to magnetically couple said magnetic-field producing means and said magnetic-field detecting means when the container is in said operative connection position.

3. The apparatus according to claim 1 wherein said magnetic-field producing means and said magnetic-field detecting means are provided on said container and body member, respectively, so that said magnetic-field producing means and said magnetic-field detecting means are not magnetically coupled when the container is in said operative connection position.

4. The apparatus according to claim 1 wherein said magnetic-field producing means establishes a unique spatial magnetic characteristic to each of the containers.

5. The apparatus according to claim 1 wherein said magnetic-field producing means is further defined as establishing a unique magnetic-field directional characteristic to each of the containers.

6. The apparatus according to claim 1 wherein said magnetic-field producing means is further defined as establishing a unique magnetic polarity characteristic to each of the containers.

7. The apparatus set forth in claim 1 wherein said magnetic-field producing means includes at least one magnetic-field producing element.

8. The apparatus according to claim 7 wherein said magnetic-field producing means includes a plurality of said magnetic-field producing elements.

9. The apparatus according to claim 8 wherein said magnetic-field detecting means includes a plurality of magnetic-field detecting elements, and wherein the number of magnetic-field detecting elements is at least equal to the number of magnetic-field producing elements.

10. The apparatus according to claim 9 wherein the number of magnetic-field detecting elements is at least twice the number of magnetic-field producing elements provided in association with each of the containers.

11. The apparatus according to claim 9 wherein the number of magnetic-field detecting elements is at least equal to the number of containers comprising said plurality of anaesthetic containers.

12. The apparatus according to claim 7 wherein said containers have a plurality of discrete locations, and wherein said plurality of discrete locations in said containers are suitable for receiving a selected number of magnetic-field producing elements.

13. The apparatus according to claim 4 wherein said magnetic-field detecting means includes a plurality of magnetic-field detecting elements, wherein said body member has a plurality of discrete locations, and wherein each of said discrete locations in said body member contains a magnetic-field detecting element.

14. The apparatus according to claim 12 wherein said magnetic-field detecting means includes a plurality of magnetic-field detecting elements, wherein said body member has a plurality of discrete locations, and wherein each of said discrete locations in said body member contains a magnetic-field detecting element.

15. The apparatus according to claim 14 wherein the selected number of magnetic-field producing elements is two or more and wherein each container has the same number of magnetic-field producing elements.

16. A method for identifying which one of a plurality of anesthetic containers containing anesthetics of different properties is connected to a connecting element of a body member of an anesthetic apparatus, said method further determining whether the container has been placed in a position in which the container has a desired operative connection to the connecting element, said method comprising the steps of:

providing a magnetic-field producing means in association with each of the containers, said magnetic-field producing means establishing a unique magnetic characteristic to each of the containers;

providing a magnetic-field detecting means in association with the body member;

bringing a selected one of the plurality of anesthetic containers into proximity with the body member to magnetically couple the magnetic-field producing means and the magnetic-field detecting means;

relatively moving at least one of the container and body member to move the container toward the operative connection position and to establish a particular magnetic coupling state between the magnetic-field producing means and the magnetic-field detecting means only when the container is in the operative connection position;

detecting, with the magnetic-field detecting means, the magnetic coupling state of the magnetic-field producing means and the magnetic field detecting means and the magnetic characteristic of the magnetic-field producing means of the container proximate to the body member;

identifying by means of the detection carried out by the magnetic-field detecting means which one of the plurality of anaesthetic containers is proximate to the body member; and determining whether the container is in the operative connection position from the magnetic coupling state of the magnetic-field producing means and the magnetic-field detecting means.

17. The method according to claim 16 wherein the step of moving the container or body member magnetically couples the magnetic-field producing means and the magnetic-field detecting means when the container is in the operative connection position.

18. The method according to claim 16 wherein the step of moving the container or body member decouples the magnetic-field producing means and the magnetic-field detecting means when the container is in the operative connection position.

19. The method according to claim 16 wherein the step of providing a magnetic-field producing means is further defined as providing a magnetic-field producing means having a unique spatial magnetic characteristic for each of the containers.

20. The method according to claim 16 wherein the step of providing a magnetic-field producing means is further defined as providing a magnetic-field producing means having a unique magnetic polarity characteristic for each of the containers.

21. The method according to claim 16 wherein the step of providing a magnetic-field producing means is further defined as providing a magnetic-field producing means having a unique magnetic-field directional characteristic for each of the containers.

22. The method according to claim 21 wherein the step of providing a magnetic-field detecting means is further defined as providing a plurality of magnetic-field detecting elements and wherein the step of detecting the magnetic characteristic is further defined as detecting the magnetic-field directional characteristic by means of a pair of the magnetic-field detecting elements.

23. The method according to claim 19 wherein the step of providing a magnetic-field producing means is further defined as providing a plurality of discrete locations in the containers and providing a selected number of magnetic-field producing elements at the plurality of discrete locations.

24. The method according to claim 23 wherein the step of providing the magnetic-field detecting means is further defined as providing a plurality of discrete locations in the connecting element and providing a magnetic-field detecting means at each of the discrete locations.

25. The method according to claim 24 wherein the step of providing a selected number of magnetic-field producing elements is further defined as providing two or more magnetic-field producing elements and as providing the same number of magnetic-field producing elements to each container of said plurality of containers.

* * * * *

UNITED STATES PATENT AND TRADEMARK OFFICE
CERTIFICATE OF CORRECTION

PATENT NO. : 5,572,992
DATED : November 12, 1996
INVENTOR(S) : Kankkunen et al

It is certified that error appears in the above-indentified patent and that said Letters Patent is hereby corrected as shown below:

CLAIM 24, Col. 10, Line 58, delete "connecting element" and substitute therefor ---body member---

Signed and Sealed this

Twenty-fifth Day of February, 1997

Attest:

BRUCE LEHMAN

*Attesting Officer*   *Commissioner of Patents and Trademarks*